United States Patent
Kiyatake et al.

(10) Patent No.: US 6,776,773 B2
(45) Date of Patent: Aug. 17, 2004

(54) LIQUID INFUSION APPARATUS

(75) Inventors: Junichi Kiyatake, Saitama (JP);
Katumi Tominaga, Saitama (JP);
Kazuhide Yamazaki, Saitama (JP);
Seiji Kojima, Saitama (JP)

(73) Assignees: Japan Servo Co., Ltd., Tokyo (JP);
Servo Techno System Co., Ltd.,
Gunma (JP); JMS Co., Ltd., Hiroshima
(JP)

(*) Notice: Subject to any disclaimer, the term of this patent is extended or adjusted under 35 U.S.C. 154(b) by 169 days.

(21) Appl. No.: 10/224,912

(22) Filed: Aug. 21, 2002

(65) Prior Publication Data

US 2003/0060768 A1 Mar. 27, 2003

(30) Foreign Application Priority Data

Aug. 30, 2001 (JP) ........................................ 2001-262090

(51) Int. Cl.[7] .............................................. A61M 5/20
(52) U.S. Cl. ................................... 604/155; 128/DIG. 1
(58) Field of Search .......................... 604/67, 154, 155, 604/207, 245; 128/DIG. 1, DIG. 12, DIG. 13

(56) References Cited

U.S. PATENT DOCUMENTS

| | | | |
|---|---|---|---|
| 4,435,173 A | | 3/1984 | Siposs et al. |
| 4,560,979 A | | 12/1985 | Rosskopf |
| 5,106,375 A | * | 4/1992 | Conero ........................ 604/155 |
| 5,545,140 A | * | 8/1996 | Conero et al. ......... 128/DIG. 1 |
| 5,647,853 A | * | 7/1997 | Feldmann et al. .......... 604/155 |
| 6,387,077 B1 | * | 5/2002 | Klibanov et al. ........... 604/155 |

FOREIGN PATENT DOCUMENTS

| | | |
|---|---|---|
| EP | 0 390 388 | 3/1990 |
| EP | 0 916 353 | 1/1998 |
| EP | 1 287 840 | 8/2002 |
| JP | 59228851 | 12/1984 |
| JP | 59228852 | 12/1984 |
| JP | 02121672 | 5/1990 |
| JP | 05042218 | 2/1993 |
| JP | 05192400 | 8/1993 |
| WO | WO 95/17914 | 7/1995 |

* cited by examiner

Primary Examiner—Anhtuan T. Nguyen
(74) Attorney, Agent, or Firm—Patterson, Thuente, Skaar & Christensen, P.A.

(57) ABSTRACT

A first sensor (13-1), the mounting position of the first sensor (13-1) being recognized as a counting number of instruction pulses to a pulse motor (3), is arranged along a plate (11) with slits of an encoder at a portion between a position where a pushing holder (7) is connected to a plunger (9) for the liquid infusion, and a start position where the pushing holder (7) is separated from the plunger (9). A counting means (16) for counting encoder pulses from the encoder, is reset when a first sensor (13-1) is detected by a position detecting device (14) moved together with the pushing holder (7), and started to count the encoder pulses according to the movement of the pushing holder (7). A time to complete the liquid infusion is calculated by using a distance between the position where the plunger (9) is connected to the holder (7) and a liquid infusion finish position proper to the syringe, and a predetermined liquid infusion speed.

13 Claims, 2 Drawing Sheets

LIQUID INFUSION APPARATUS

BACKGROUND OF THE INVENTION

1. Field of the Invention

The present invention relates to a liquid infusion apparatus and, more particularly, relates to a liquid infusion apparatus for infusing liquid by pushing a plunger into a syringe.

2. Description of the Prior Art

FIG. 1 shows a conventional liquid infusion apparatus. In FIG. 1, reference numeral 1 denotes a CPU, 2 denotes a processing circuit of a signal from an incremental linear encoder, 3 denotes a synchronous pulse motor, 4 denotes a reduction gear, 5 denotes a feed screw, 6 denotes a carriage, 7 denotes a pushing holder fixed to the carriage 6, for pushing a plunger 9 of a syringe 8, 10 denotes a processing circuit of a sensing signal from an established position detecting sensor 13 positioned at a remaining infusion liquid quantity small section, 11 denotes an elongated opaque plate with fine slits for forming an incremental linear encoder, arranged in parallel to the feed screw 5, 12 denotes a photo-coupler mounted on the carriage 6 for detecting pulses from the incremental linear encoder, 14 denotes an established position detecting dog connected to the carriage 6, 15 denotes an instruction pulse counter for counting instruction pulses to the pulse motor 3, 16 denotes a pulse counter for counting pulses from the incremental linear encoder, and 17 denotes a driving circuit for the synchronous pulse motor 3.

In such conventional liquid infusion apparatus, an output from the photo-coupler 12 is applied to the pulse counter 16 through the processing circuit 2, and an output from the established position detecting sensor 13 is applied to the CPU 1 through the processing circuit 10. The pulse counters 15 and 16 are monitored and managed by the CPU 1.

The driving circuit 17 receives from the CPU 1 instructions indicating a distance to be moved by the motor 3 and a speed etc. of the motor 3, and drives the motor 3. The carriage 6 is moved by the motor 3 through the reduction gear 4 and the feed screw 5. A pulse signal generated by the incremental linear encoder and picked up by the photo-coupler 12 is processed by the processing circuit 2 and sent to the pulse counter 16 as a moving information of the carriage 6, so that the motion of the carriage 6 is monitored directly by the CPU 1.

A value of the moving instruction recognized by monitoring the instruction pulse counter 15 per unit time is compared with an actual moving distance recognized by monitoring the encoder pulse counter 16, so that a correlation state between the value of the moving instruction and the actual moving distance can be detected.

If the correlation state is maintained, it is recognized that the pushing holder 7 is moved correctly according to the instruction.

The output from the established position detecting sensor 13, which is generated when the established position detecting dog 14 mounted on the carriage 6 passes across the established position detecting sensor 13 during the liquid infusion operation, is processed by the processing circuit 10 and sent to the CPU 1 as a position information. When the position information from the established position detecting sensor 13 is applied to the CPU 1, a counted value in the instruction pulse counter 15 is memorized in the CPU 1, or the pulse counter 15 is reset by the CPU 1. Then, instruction pulses sent from the driving circuit 17 to the synchronous pulse motor 3 are counted by the instruction pulse counter 15. Each of the instruction pulses sent to the motor 3 corresponds to a distance moved actually by the pulse motor 3, so that the absolute position of the pushing holder 7 and thus the absolute position of the plunger 9 engaged with the pushing holder 7 can be recognized by counting the instruction pulses sent to the motor 3 by the instruction pulse counter 15.

In such conventional liquid infusion apparatus, the absolute position of the pushing holder 7 can be recognized after the established position detecting dog 14 is passed across the established position detecting sensor 13 during the liquid infusion operation by counting the pulses sent to the pulse motor 3, so that information about the warning for the remaining infusion liquid quantity small section, and information about the finish of the liquid infusion operation can be obtained.

Further, in the conventional liquid infusion apparatus, operation steps, such as the start and stop of the liquid infusion operation are indicated by the LED or liquid crystal. The erroneous operation can be informed by a sound of beep or melody.

In the above described conventional liquid infusion apparatus, however, the absolute position of the pushing holder 7 can be recognized only when the established position detecting sensor 13 is detected by the established position detecting dog 14 during the liquid infusion operation by the motor 3 driven by the instruction pulses. Accordingly, the information about the finish of the liquid infusion operation cannot be obtained when the liquid infusion operation is started.

Further, the operator cannot recognize the kinds of error even if the sound of beep or the melody is generated. Accordingly, the operator has to approach the small indicator of the liquid infusion apparatus in order to recognize the contents or kinds of the warning and it is troublesome.

SUMMARY OF THE INVENTION

In order to solve the forgoing problems in the conventional liquid infusion apparatus, it is an object of the present invention to provide a liquid infusion apparatus comprises a pushing holder for pushing a plunger into a cylinder of a syringe, a pulse motor for moving the pushing holder, an incremental linear encoder having a plate with slits arranged along a moving direction of the plunger and a position detecting device moved together with the pushing holder, counting means for counting encoder pulses from the encoder, means for counting instruction pulses to the pulse motor, and a first sensor, the mounting position of the first sensor being recognized as a counting number of instruction pulses to the pulse motor, wherein the first sensor is arranged along the plate with slits at a portion between a position where the pushing holder is connected to the plunger for the liquid infusion, and a start position where the pushing holder is separated from the plunger, wherein the counting means is reset when the first sensor is detected by the position detecting device, and started to count the encoder pulses according to the movement of the pushing holder, and wherein a time to complete the liquid infusion is calculated by using a distance between the position where the plunger is connected to the holder and a liquid infusion finish position proper to the syringe, and a predetermined liquid infusion speed, and displayed.

Another object of the present invention to provide a liquid infusion apparatus wherein a time to complete the liquid infusion is calculated by using a predetermined liquid infusion speed and a distance between a present position of the holder and a liquid infusion finishing position proper to the syringe determined previously, and displayed, the present position of the holder being obtained by summing a moving distance recognized as the count number of the instructing pulses to be sent to the motor and a position of the holder recognized as the count number of the encoder pulses at the start of the liquid infusion.

Further object of the present invention to provide a liquid infusion apparatus, further comprising at least one second sensor provided along a moving path of the pushing holder for liquid infusion, the position of the second sensor being recognized as a count number of the instruction pulses to the motor, wherein when the second sensor is detected by the position detecting device, the present position of the pushing holder is revised automatically to a position data of the second sensor, and thereafter the position of the pushing holder is determined by using a count number of the instruction pulses to the motor which is more precisely than the encoder pulses.

Still further object of the present invention to provide a liquid infusion apparatus, further comprising a chronometer element which can recognize the present hour, wherein an expected liquid infusion finishing hour can be calculated and displayed by using the present hour and a time to complete the liquid infusion.

Yet further object of the present invention to provide a liquid infusion apparatus, further comprising a sound display device, wherein a time to complete the liquid infusion or an expected finish hour can be indicated by a voice.

Still another object of the present invention to provide a liquid infusion apparatus, further comprising setting means for setting operation orders of liquid infusion, means for indicating the operation orders by a voice, means for comparing actual operation orders with the operation orders predetermined by the setting means, and means for indicating a difference by a voice when actual operation orders are different from the predetermined operation orders.

These and other aspects and objects of the present invention will be better appreciated and understood when considered in conjunction with the following description and the accompanying drawings. It should be understood, however, that the following description, while indicating preferred embodiments of the present invention, is given by way of illustration and not of limitation. Many changes and modifications may be made within the scope of the present invention without departing from the spirit thereof, and the invention includes all such modifications.

DESCRIPTION OF THE PREFERRED EMBODIMENTS

Figure 1:
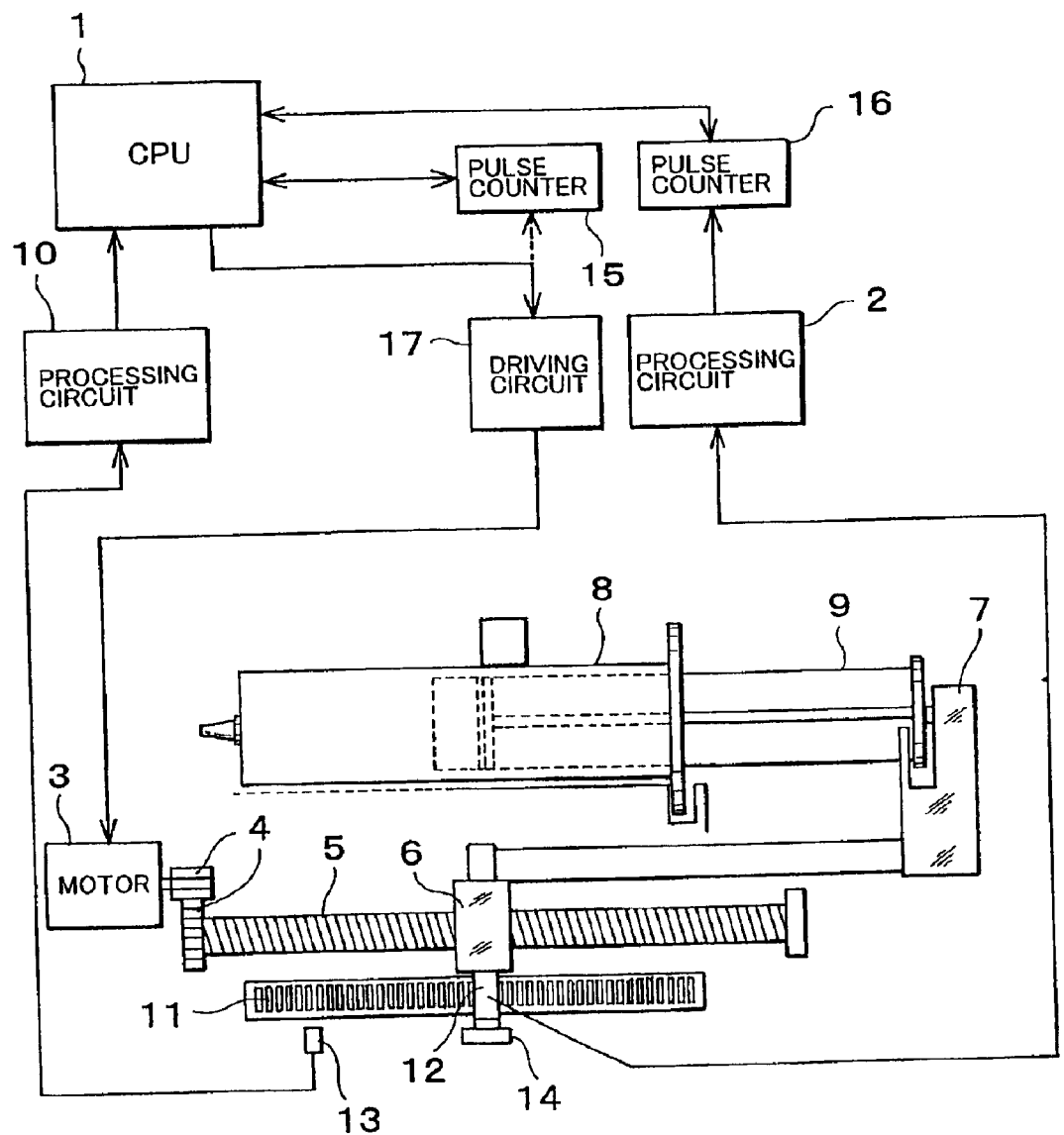
FIG. 1 is an explanation view of a conventional liquid infusion apparatus.

A first invention of the present invention will now be explained with reference to FIG. 2. Constructional parts shown in FIG. 2 which are similar to corresponding parts of the liquid infusion apparatus shown in FIG. 1 are indicated at like reference characters, and the detailed explanation thereof is omitted.

Figure 2:
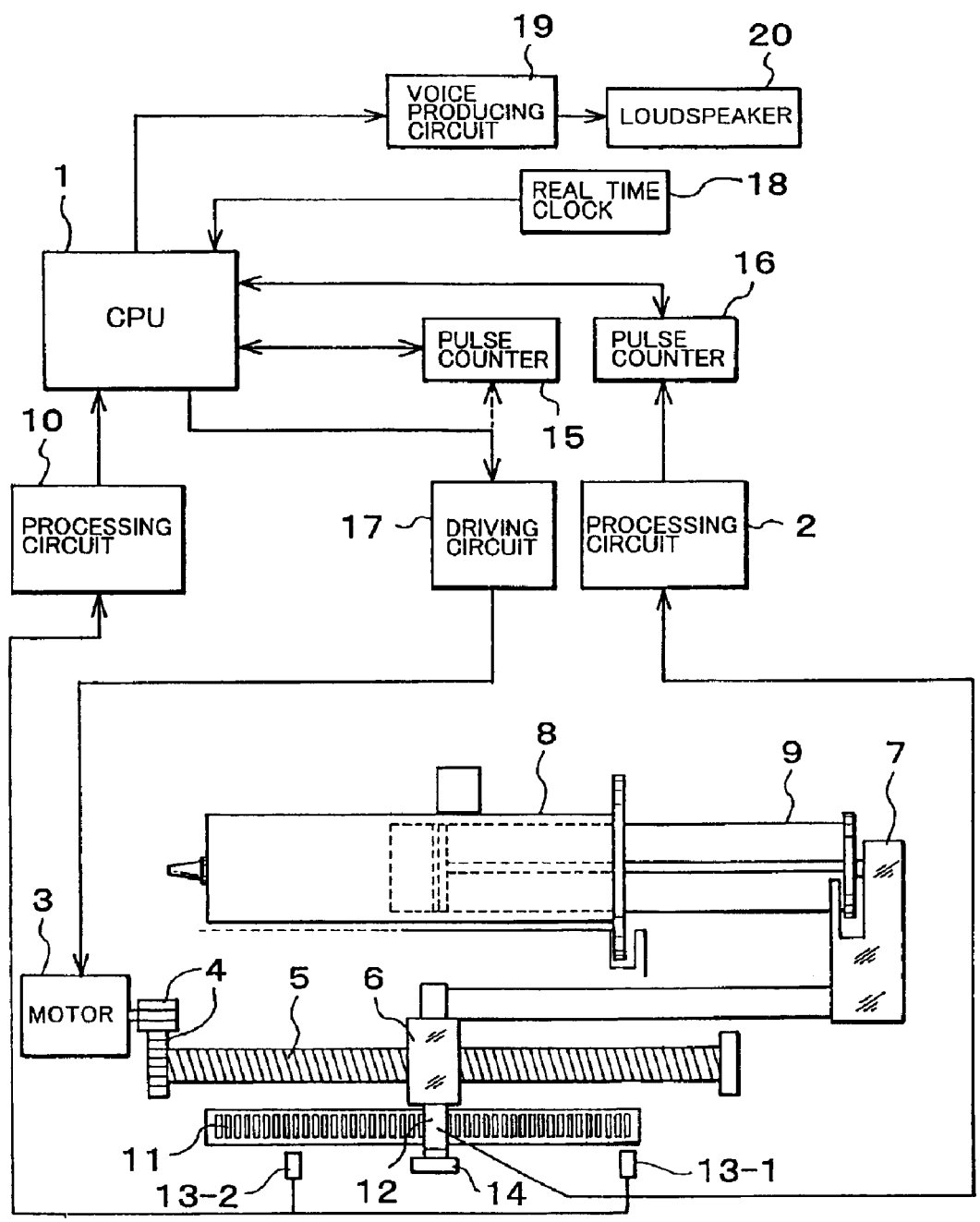
FIG. 2 is an explanation view of a liquid infusion apparatus in accordance with the present invention.

In the present invention as shown in FIG. 2, a first sensor 13-1, the position of which is recognized as a counted value of the pulse counter 15 for counting instruction pulses to the motor 3, is arranged at a first position near one end portion of the plate 11 with slits.

The pushing holder 7 is moved by hand rightward separating from the plunger 9 and set to a start position. The first position of the first sensor 13-1 corresponds to a portion between a position where the pushing holder 7 is connected to the plunger 9 for starting the liquid infusion and the start position of the pushing holder 7. Accordingly, when the pushing holder 7 moves leftwards from the start position thereof, the dog 14 is passed across the first sensor 13-1, so that the pulse counter 16 of the incremental linear encoder is cleared by the processing circuit 2. When the pushing holder 7 is moved leftwards further, the counter 16 counts pulses of the incremental linear encoder and when the plunger 9 is set to the pushing holder 7, the counted value of the counter 16 is stored to recognize the absolute position of the plunger 9 set to the pushing holder 7 as the encoder plus number.

A time to complete the liquid infusion from the starting time of the liquid infusion, is calculated by using a predetermined liquid infusion speed and a distance between the recognized absolute position of the plunger 9 connected to the holder 7 and a liquid infusion finishing position proper to the syringe 8 determined previously as the number of the instructing pulses to be sent to the motor 3, and displayed.

A push button (not shown) is provided for recognizing a remaining infusion liquid quantity, so that when this button is pushed during the liquid infusion operation, a time to complete the liquid infusion is calculated and displayed. The time can be calculated by using a moving distance of the pushing holder 7 recognized as the instruction pulses to the motor 3 counted by the instruction pulse counter 15, a distance from the present position of the pushing holder 7 recognized as the counted value of the pulse counter 16 to a previously calculated liquid infusion complete position proper to the mounted syringe 8, and a predetermined speed of the liquid infusion.

A second sensor 13-2, the position of which is recognized as a counted value of the pulse counter 15 for counting instruction pulses to the motor 3, is arranged at a second position near the other end of the plate 11. The second position of the second sensor 13-2 corresponds to a position on the plate 11 corresponding to the liquid infusion operation section after the start of the liquid infusion. When the established position detecting dog 14 is moved leftwards across the second sensor 13-2, the position of the pushing holder 7 is revised automatically to a position determined by the position data of the second sensor 13-2. Then, a time to complete the liquid infusion, is calculated precisely by determining the position of the pushing holder 7 by using the instruction pulses to the motor 3 which is more precisely than the encoder pulses, and displayed.

A real time clock 18 consisting of a chronometer element which can recognize the present hour is provided to calculate and display an expected liquid infusion finishing hour by using the present hour and a time to complete the liquid infusion.

Further, a display device having a voice producing circuit 19 controllable by the CPU 1 and a loudspeaker 20 is provided so as to indicate by a voice a time to finish the liquid infusion or a finish hour.

An another embodiment of a liquid infusion apparatus according to the present invention comprises setting means for setting operation steps of liquid infusion, means for indicating the operation orders by using a voice, and means for comparing actual operation orders with the operation orders predetermined by the setting means, wherein when the actual operation orders are different from the predetermined operation orders, the difference is indicated by a loudspeaker etc. to an operator.

Further, the guide or warning of the operation orders, the contents of the warning, information of the operation time or the expected finish hour of the operation etc. can be informed by using a voice to the operator.

According to the liquid infusion apparatus of the present invention, the moving distance and the absolute position of the carriage for pushing the plunger can be detected by a simple construction, so that the time to complete the liquid infusion can be determined. Accordingly, the finish time of day of the liquid information can be calculated and displayed correctly by using the moving distance and the liquid infusion speed. Further, the error of the operation orders etc. can be indicated by using a voice, so that operator can take suitable operations.

While the invention has been particularly shown and described with reference to the preferred embodiments thereof, it will be understood by those skilled in the art that various changes in form and details may be made therein without departing from the spirit and scope of the invention as defined by the appended claims.

What is claimed is:

1. A liquid infusion apparatus comprising a pushing holder for pushing a plunger into a cylinder of a syringe, a pulse motor for moving the pushing holder, an incremental linear encoder having a plate with slits arranged along a moving direction of the plunger and a position detecting device moved together with the pushing holder, counting means for counting encoder pulses from the encoder, means for counting instruction pulses to the pulse motor, and a sensor, the mounting position of the sensor being recognized as a counting number of instruction pulses to the pulse motor, wherein the sensor is arranged along the plate with slits at a portion between a position where the pushing holder is connected to the plunger for the liquid infusion, and a start position where the pushing holder is separated from the plunger, wherein the counting means is reset when the sensor is detected by the position detecting device, and started to count the encoder pulses according to the movement of the pushing holder, and wherein a time to complete the liquid infusion is calculated by using a distance between the position where the plunger is connected to the holder and a liquid infusion finish position proper to the syringe, and a predetermined liquid infusion speed, and displayed.

2. The liquid infusion apparatus as claimed in claim 1, wherein a time to complete the liquid infusion is calculated by using a predetermined liquid infusion speed and a distance between a present position of the holder and a liquid infusion finishing position proper to the syringe determined previously, and displayed, the present position of the holder being obtained by summing a moving distance recognized as the count number of the instructing pulses to be sent to the motor and a position of the holder recognized as the count number of the encoder pulses at the start of the liquid infusion.

3. The liquid infusion apparatus as claimed in claim 1, further comprising at least one additional sensor provided along a moving path of the pushing holder for liquid infusion, the position of the additional sensor being recognized as a count number of the instruction pulses to the motor, wherein when the additional sensor is detected by the position detecting device, the present position of the pushing holder is revised automatically to a position data of the additional sensor, and thereafter the position of the pushing holder is determined by using a count number of the instruction pulses to the motor which is more precisely than the encoder pulses.

4. The liquid infusion apparatus as claimed in claim 2, further comprising at least one additional sensor provided along a moving path of the pushing holder for liquid infusion, the position of the additional sensor being recognized as a count number of the instruction pulses to the motor, wherein when the additional sensor is detected by the position detecting device, the present position of the pushing holder is revised automatically to a position data of the additional sensor, and thereafter the position of the pushing holder is determined by using a count number of the instruction pulses to the motor which is more precisely than the encoder pulses.

5. The liquid infusion apparatus as claimed in claim 1, further comprising a chronometer element which can recognize the present hour, wherein an expected liquid infusion finishing hour can be calculated and displayed by using the present hour and a time to complete the liquid infusion.

6. The liquid infusion apparatus as claimed in claim 2, further comprising a chronometer element which can recognize the present hour, wherein an expected liquid infusion finishing hour can be calculated and displayed by using the present hour and a time to complete the liquid infusion.

7. The liquid infusion apparatus as claimed in claim 3, further comprising a chronometer element which can recognize the present hour, wherein an expected liquid infusion finishing hour can be calculated and displayed by using the present hour and a time to complete the liquid infusion.

8. The liquid infusion apparatus as claimed in claim 1, further comprising a sound display device, wherein a time to complete the liquid infusion or an expected finish hour can be indicated by a voice.

9. The liquid infusion apparatus as claimed in claim 2, further comprising a sound display device, wherein a time to complete the liquid infusion or an expected finish hour can be indicated by a voice.

10. The liquid infusion apparatus as claimed in claim 3, further comprising a sound display device, wherein a time to complete the liquid infusion or an expected finish hour can be indicated by a voice.

11. The liquid infusion apparatus as claimed in claim 1, further comprising setting means for setting operation orders of liquid infusion, means for indicating the operation orders by a voice, means for comparing actual operation orders with the operation orders predetermined by the setting means, and means for indicating a difference by a voice when actual operation orders are different from the predetermined operation orders.

12. The liquid infusion apparatus as claimed in claim 2, further comprising setting means for setting operation orders of liquid infusion, means for indicating the operation orders by a voice, means for comparing actual operation orders with the operation orders predetermined by the setting means, and means for indicating a difference by a voice when actual operation orders are different from the predetermined operation orders.

13. The liquid infusion apparatus as claimed in claim 3, further comprising setting means for setting operation orders of liquid infusion, means for indicating the operation orders by a voice, means for comparing actual operation orders with the operation orders predetermined by the setting means, and means for indicating a difference by a voice when actual operation orders are different from the predetermined operation orders.

* * * * *